(12) United States Patent
Murakami et al.

(10) Patent No.: US 10,544,098 B2
(45) Date of Patent: Jan. 28, 2020

(54) METHOD FOR SYNTHESIZING BIPYRIDINE COMPOUND AND METHOD FOR MANUFACTURING PYRIDINE COMPOUND

(71) Applicant: KOBELCO ECO-SOLUTIONS CO., LTD., Hyogo (JP)

(72) Inventors: Yoshiaki Murakami, Hyogo (JP); Yukihiro Goto, Hyogo (JP); Miyuki Fukushima, Hyogo (JP); Kazuhiko Takai, Okayama (JP); Sobi Asako, Okayama (JP)

(73) Assignee: Kobelco Eco-Solutions Co., Ltd., Hyogo (JP)

(*) Notice: Subject to any disclaimer, the term of this patent is extended or adjusted under 35 U.S.C. 154(b) by 0 days.

(21) Appl. No.: 15/766,075

(22) PCT Filed: Oct. 7, 2016

(86) PCT No.: PCT/JP2016/079887
§ 371 (c)(1),
(2) Date: Apr. 5, 2018

(87) PCT Pub. No.: WO2017/061581
PCT Pub. Date: Apr. 13, 2017

(65) Prior Publication Data
US 2018/0282278 A1    Oct. 4, 2018

(30) Foreign Application Priority Data

Oct. 8, 2015  (JP) .................. 2015-200412
Feb. 1, 2016  (JP) .................. 2016-017237
Mar. 11, 2016 (JP) .................. 2016-048472

(51) Int. Cl.
*C07D 213/22*   (2006.01)
*C07D 213/127*  (2006.01)
*B01D 9/00*     (2006.01)
*B01J 23/04*    (2006.01)

(52) U.S. Cl.
CPC ......... *C07D 213/22* (2013.01); *B01D 9/0004* (2013.01); *B01D 9/005* (2013.01); *C07D 213/127* (2013.01); *B01J 23/04* (2013.01)

(58) Field of Classification Search
None
See application file for complete search history.

(56) References Cited

U.S. PATENT DOCUMENTS

| | | |
|---|---|---|
| 2,773,066 A | 12/1956 | Linnell et al. |
| 3,227,723 A | 1/1966  | Baines et al. |
| 4,177,349 A | 12/1979 | McGill |
| 4,424,359 A | 1/1984  | Kaschig et al. |
| 5,294,376 A | 3/1994  | Byker |

FOREIGN PATENT DOCUMENTS

| | | |
|---|---|---|
| CN | 1158852 A   | 9/1997 |
| CN | 1443758 A   | 9/2003 |
| CN | 104910892 A | 9/2015 |
| JP | 57-64672 A  | 4/1982 |
| JP | 2006-219395 A | 8/2006 |

OTHER PUBLICATIONS

Fu et al., "Intra- and Intermolecular C—H Activation by Bis(phenolate)pyridineiridium(III) Complexes," Organometallics, 30: 6751-6765 (2011).
Buonomo et al., "Substituted 2, 2'-bipyridines by nickel-catalysis: 4, 4'-di-tert-butyl-2,2'-bipyridine," Synthesis (Stuttg), 45:(22), 3099-3102 (Nov. 1, 2013).
Wang et al., "A New Synthetic Method of Bipyridines," Qingdao Daxue Xuebao, Gongcheng Jishuban, 10(2): 25-28 (1995).
Huenig et al., "A convenient synthesis of 2,2', 6,6'-tetramethyl-4,4'-bipyridine and its oxidation to 2,2', 6,6'-tetracarboxy-4,4'-bipyridine," Synthesis, 7: 552-554 (1989).
Setton, "Action of Sodium on pyridine." Compt. rend. 244: 1205-1207 (1957).
Tolkacheva et al., "Reaction of pyridine with metallic lithium," Sb. Nauch. Tr. Tashkent. Un-t, (1978) 553: 42-46; From: Ref. Zh., Khim.; Abstract No. 12B1070 (1979).
Eliu-Ceausescu, "Mathematical model of the chance behavior of chemical reactors. 1. Multidimensional variance analytical model of an organometallic reaction," Analele Universitatii din Timisoara, Stiinte Fizice-Chimice 17(2): 25-32 (1979).
Ziyaev et al., "Dimerization of some β-substituted pyridine bases in the presence of metallic sodium and Raney nickel catalysts," Izvestiya Akademii Nauk SSSR, Seriya Khimicheskaya 11: 2607-2611 (1983).
Ogata, Kagaku Jikken Sosaho first volume, 27th Edition, Nankodo Co., Ltd., pp. 366-399 (1963).
Edited by the Chemical Society of Japan, Kagaku Binran Oyo Kagaku Hen 6th edition, Chapter 4, Kagaku Gosei Gijutsu, Maruzen Co., Ltd., p. 178 (2003).
Edited by the Chemical Society of Japan, 4th edition Jikken Kagaku Koza 1 Kihon Sosa I, Maruzen Co., Ltd., pp. 184-189 (1990).
Asahara, Yozai Handbook, Kodansha Ltd., pp. 47-51(1985).
Edited by The Chemical Society of Japan, Jikken Kagaku Guidebook, 3rd edition, Maruzen Co., Ltd., pp. 130-131 (1992).
Bossmann et al., "Synthesis of Crown-ester-Bipyridines and Crown-Ester-Viologens," Synthesis, 2005, No. 6, pp. 907-914.
Soto et al, "A Non-Covalent Strategy for the Assembly of Supramolecular Photocurrent-Generating Systems," J. Am. Chem. Soc., 2003, No. 125, Mar. 12, 2003, pp. 2838-2839 and Supporting Information.
Extended European Search Report dated Feb. 26, 2019.
English translation of International Preliminary Report on Patentability dated Apr. 19, 2018 (Forms PCT/IB/338, PCT/IB/373 & PCT/ISA/237).
Brown et al, "Preparation and Reactions of 2,6-Di-t-butylpyridine and Related Hindered Bases. A Case of Steric Hindrance toward the Proton," Journal of the American Chemical Society 88(5), Mar. 5, 1966, pp. 986-992.
Japanese Office Action dated Jun. 12, 2018.

*Primary Examiner* — Zinna Northington Davis
(74) *Attorney, Agent, or Firm* — Dilworth & Barrese, LLP

(57) ABSTRACT

A target bipyridine compound is synthesized with high purity and a high yield in a simple and safe manner in a short period of time. A method for synthesizing a di-tert-butyl-2, 2'-bipyridine compound is provided, and the method includes a step of reacting, in a reaction solvent, a tert-butylpyridine compound with a dispersion product obtained by dispersing an alkali metal in a dispersion solvent. A method for synthesizing a bipyridine compound having no substituents is also provided, and the method includes a step of reacting, in a reaction solvent, pyridine with a dispersion product obtained by dispersing an alkali metal in a dispersion solvent.

8 Claims, 6 Drawing Sheets

Fig.1

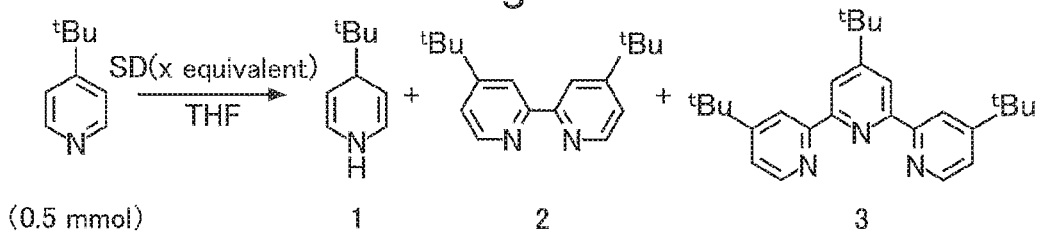

(0.5 mmol)

| Experiment No. | THF (ml) | SD* | Temperature (°C) | Time (hours) | Yield(%) Compound1 | Yield(%) Compound2 | Yield(%) Compound3 | Recovery rate (%) |
|---|---|---|---|---|---|---|---|---|
| 1 | 1 | 2.5 | 50 | 2 | 0 | 55 | 2 | 3 |
| 2 | 1 | 1 | 50 | 2 | 0 | 48 | 6 | Extremely small amount |
| 3 | 1 | 1 | 25 | 2 | 0 | 50 | 0 | 28 |
| 4 | 1 | 1 | 25 | 6 | 0 | 57 | 2 | 6 |
| 5 | 1 | 1 | 0 | 2 | 0 | 3 | 0 | 90 |

*Represented in molar equivalent with respect to 4-tert-butylpyridine.

Fig.2

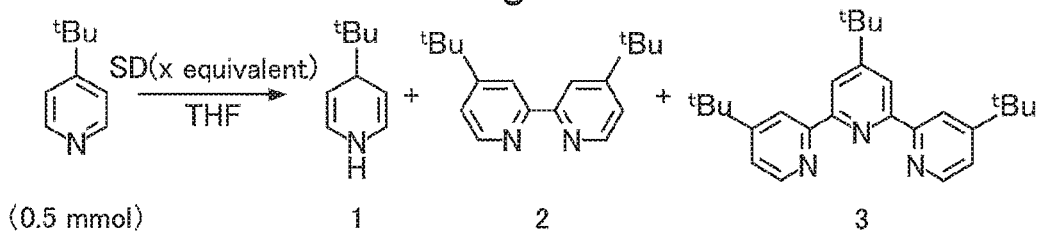

(0.5 mmol)

| Experiment No. | THF (ml) | SD* | Temperature (°C) | Time (hours) | Yield(%) Compound1 | Yield(%) Compound2 | Yield(%) Compound3 | Recovery rate (%) |
|---|---|---|---|---|---|---|---|---|
| 1 | 2 | 1 | 50 | 1 | 0 | 68 | 0 | 10 |
| 2 | 2 | 1 | 50 | 2 | 0 | 78 | 0 | 25 |
| 3 | 2 | 1 | 50 | 6 | 0 | 80 | 0 | 3 |
| 4 | 2 | 1 | 25 | 6 | 0 | 74 | 2 | 17 |
| 5 | 2 | 1 | 25 | 24 | 0 | 78 | 9 | 1 |
| 6 | 2 | 2 | 25 | 6 | 0 | 43 | 1 | 3 |
| 7 | 4 | 1 | 25 | 6 | 0 | 64 | 0 | 22 |
| 8 | 4 | 1 | 25 | 24 | 0 | 57 | 0 | 27 |
| 9 | 4 | 2 | 25 | 6 | 0 | 67 | 1 | 10 |

*Represented in molar equivalent with respect to 4-tert-butylpyridine.

| Experiment No. | Reaction time (hours) | Yield(%) Compound1 | Yield(%) Compound2 | Recovery rate (%) |
|---|---|---|---|---|
| 1 | 1 | 0 | 20 | 5 |
| 2 | 2 | 0 | 46 | 13 |

(0.5 mmol)

| Experiment No. | R | THF (ml) | Temperature (°C) | Time (hours) | Yield(%) Compound1 | Yield(%) Compound2 | Recovery rate (%) |
|---|---|---|---|---|---|---|---|
| 1 | Methyl group | 1 | 25 | 2 | 0 | 0 | 33 |
| 2 | Methyl group | 1 | 50 | 2 | 0 | 3 | 6 |
| 3 | Methyl group | 2 | 25 | 6 | 0 | Extremely small amount | 17 |
| 4 | Methyl group | 2 | 50 | 6 | 0 | 3 | 4 |
| 5 | Phenyl group | 1 | 25 | 2 | 0 | 4 | 77 |
| 6 | Phenyl group | 1 | 50 | 2 | 0 | 0 | 99 |
| 7 | Dimethylamino group | 1 | 25 | 2 | 0 | 0 | 81 |
| 8 | Dimethylamino group | 1 | 50 | 2 | 0 | 2 | 50 |

| Experiment No. | Reaction solvent Type | Reaction solvent (ml) | SD* | Temperature (°C) | Time (hours) | Presence ratio of product(%) Compound1 | Presence ratio of product(%) Compound2 |
|---|---|---|---|---|---|---|---|
| 1 | THF:EDA=1:1 | 1 | 2 | 25 | 3 | 62.11 | 37.89 |

*Represented in molar equivalent with respect to pyridine.

METHOD FOR SYNTHESIZING BIPYRIDINE COMPOUND AND METHOD FOR MANUFACTURING PYRIDINE COMPOUND

TECHNICAL FIELD

The present invention relates to a method for synthesizing a bipyridine compound and a method for manufacturing a pyridine compound.

BACKGROUND ART

Bipyridine compounds are known to be useful as catalysts and organic materials, and can form complexes with various transition metals. For example, bipyridine compounds are used in a large number of chemical reactions such as a magnesium-catalyzed carbon dioxide reduction reaction, an iridium-catalyzed C—H boration reaction, and a nickel-catalyzed electrophilic cross-coupling reaction. In addition, bipyridine compounds are known to be useful as intermediates and raw materials of organic electroluminescence (organic EL) materials, pharmaceuticals, agricultural chemicals, and the like.

As a method for synthesizing a bipyridine compound, a method is reported in which 4-tert-butylpyridine-N-oxide is synthesized by reacting 4-tert-butylpyridine and peracetic acid, 4-tert-butyl-2-chloropyridine is synthesized by reacting 4-tert-butylpyridine-N-oxide with phosphoryl chloride and substituting hydrogen at 2-position with chlorine, and then 4,4'-di-tert-butyl-2,2'-bipyridine is synthesized through dimerization of 4-tert-butyl-2-chloropyridine performed in the presence of nickel bromide and a manganese catalyst (see Non-Patent Documents 1 and 2, for example).

In addition, as a method for manufacturing 2,4'-bipyridine, a technique is known in which 4-pyridylboronic acid and 2-chloropyridine are reacted using a butanol solvent in the presence of a palladium catalyst, sodium carbonate, and water, and the reaction mixture is separated into an organic layer containing 2,4'-bipyridine and an aqueous layer through liquid-liquid separation (see Example 1 in Patent Document 1, for example). A technique is disclosed in which thereafter, 2,4'-bipyridine is purified by extracting the water layer with butanol, mixing the resultant butanol layer with the previous organic layer, washing the mixed organic layer using water followed by filtration, concentrating the obtained filtrate, and distilling this concentrated solution (see Example 11). Patent Document 1 states that the purity is 98.5% and the collection yield is 47% as a result of this process.

CITATION LIST

Patent Literature

Patent Document 1: JP 2006-219395A Non-Patent Literature

Non-Patent Document 1: Fu R, Bercaw J E, Labinger J A., Organometallics. 2011; 30: 6751-6765

Non-Patent Document 2: Buonomo J A., Everson D A., Weix D J., Synthesis (Stuttg). 2013; 45(22): 3099-3102

SUMMARY OF INVENTION

Technical Problem

However, in the synthesis methods disclosed in Non-Patent Documents 1 and 2, peracetic acid, which is highly explosive under a concentrated condition, is used, and is removed through distillation after 4-tert-butylpyridine-N-oxide is synthesized, and it is thus necessary to perform operations that are extremely difficult to handle and are complicated. In addition, no less than three days are required for merely the reaction. Regarding the yields, in the synthesis of 4-tert-butylpyridine-N-oxide from 4-tert-butylpyridine, 4-tert-butyl-2-chloropyridine from 4-tert-butylpyridine-N-oxide, and 4,4'-di-tert-butyl-2,2'-bipyridine from 4-tert-butyl-2-chloropyridine, the compounds are obtained at yields of 82%, 79%, and 90%, respectively, and the final yield is about 58%.

In the manufacturing method disclosed in Patent Document 1, a catalyst is used to synthesize a pyridine compound, thus increasing production man-hours. In addition, an expensive palladium catalyst is used, thus increasing production cost. Furthermore, in distillation treatment, evaporation and condensation are performed utilizing the differences between the boiling points of various organic substances contained in a filtrate, and therefore, a large amount of labor is required to collect the target pyridine compound with a good yield.

Therefore, there is a demand for the development of a technique according to which it is possible to synthesize a bipyridine compound with high purity and a high yield in a simple and safe manner in a short period of time. Moreover, there is a demand for a method for manufacturing a pyridine compound according to which it is possible to synthesize a pyridine compound at low cost with reduced production man-hours and to collect the synthesized pyridine compound efficiently.

Solution to Problem

As a result of performing intensive studies to solve the above-mentioned problems, the inventors of the present invention found that a target bipyridine compound can be synthesized with high purity and a good yield by reacting a pyridine compound with a dispersion product obtained by dispersing an alkali metal in a dispersion solvent. In such a synthesis reaction, agents that are difficult to handle are not needed, and complicated operations are not performed. Moreover, the target bipyridine compound can be synthesized in a simple manner in a short period of time through a small number of steps. The inventors of the present invention achieved the present invention based on these findings.

Specifically, a feature of a method for synthesizing a di-tert-butyl-2,2'-bipyridine compound represented by General Formula (I) below according to the present invention is that the method includes a step of reacting, in a reaction solvent, a tert-butylpyridine compound with a dispersion product obtained by dispersing an alkali metal in a dispersion solvent.

Chemical Formula 1

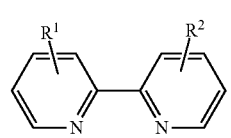

General Formula (I)

(In this formula, $R^1$ and $R^2$ are independently tert-butyl groups.)

With the synthesis methods disclosed in Non-Patent Documents 1 and 2,4-tert-butyl-2-chloropyridine is synthesized by reacting a chlorinating agent with 4-tert-butylpyridine-N-oxide obtained through oxidation of 4-tert-butylpyridine using peracetic acid, and a bipyridine ring is formed through dimerization of 4-tert-butyl-2-chloropyridine. However, there are disadvantages in that the handling of peracetic acid needs to be taken care of under a concentrated condition, a step of removing peracetic acid through distillation is required, and the reaction requires a long period of time. In contrast, with the above-mentioned configuration, the dispersion product obtained by dispersing an alkali metal in a dispersion solvent is used. Thus, the easy handling is achieved, and the pyridine ring dimerization reaction can progress smoothly and efficiently. As a result, it is not necessary to perform complicated reaction operations and to use agents that are highly explosive. Accordingly, the target di-tert-butyl-2,2'-bipyridine compound can be synthesized with high purity and a high yield in a simple and safe manner in a short period of time.

Another feature is that a hydrogen donor is added to a reaction product produced through the reaction of the tert-butylpyridine with the dispersion product obtained by dispersing an alkali metal in a dispersion solvent.

With this configuration, after the reaction of the tert-butylpyridine with the dispersion product obtained by dispersing an alkali metal in a dispersion solvent, the hydrogen donor and the reaction product are reacted. Accordingly, the dimerization of the pyridine ring and the acceptance of hydrogen from the hydrogen donor can progress smoothly in succession, thus making it possible to synthesize the target di-tert-butyl-2,2'-bipyridine compound with high purity and a high yield.

Another feature is that the reaction solvent contains a hydrogen donor.

With this configuration, a combined solution is formed by adding the hydrogen donor to the reaction solvent, which is a reaction site in which the tert-butylpyridine compound and the dispersion product obtained by dispersing an alkali metal in a dispersion solvent are reacted. Accordingly, it is not necessary to additionally perform a step of adding the hydrogen donor, thus making it possible to simplify the synthesis process. As a result, the target di-tert-butyl-2,2'-bipyridine compound can be synthesized in a simple manner through a small number of steps, thus making it possible to reduce production cost.

Another feature is that the tert-butylpyridine compound is 4-tert-butylpyridine, and 4,4'-di-tert-butyl-2,2'-bipyridine is synthesized.

With this configuration, 4-tert-butylpyridine is used as a starting compound. Accordingly, 4,4'-di-tert-butyl-2,2'-bipyridine, which is of particularly high utility value as a catalyst and an organic material, can be synthesized with high purity and a high yield in a simple and safe manner in a short period of time.

Another feature is that when a ratio of tetrahydrofuran serving as the reaction solvent with respect to 1 mmol of the tert-butylpyridine compound is set to 2 ml or more and 8 ml or less, the alkali metal is used in an amount of 1 mol equivalent or more and 2.5 mol equivalents or less with respect to the tert-butylpyridine compound.

With this configuration, the usage amount of the dispersion product obtained by dispersing an alkali metal in a dispersion solvent and the usage amount of tetrahydrofuran serving as the reaction solvent can be optimized with respect to the tert-butylpyridine compound used as the starting compound, and the reactions progress smoothly in succession. Accordingly, the generation of reaction by-products can be suppressed, and the target di-tert-butyl-2,2'-bipyridine compound can be synthesized with high purity and a high yield. In addition, the raw materials can be used in the correct amounts in the synthesis, thus making it possible to synthesize the target di-tert-butyl-2,2'-bipyridine compound with a favorable material balance.

Another feature is that a method for synthesizing a bipyridine compound represented by General Formula (II) below includes a step of reacting, in a reaction solvent, pyridine with a dispersion product obtained by dispersing an alkali metal in a dispersion solvent.

Chemical Formula 2

General Formula (II)

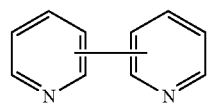

With this configuration, the dispersion product obtained by dispersing an alkali metal in a dispersion solvent is used. Thus, easy handling is achieved, and the pyridine ring dimerization reaction can progress smoothly and efficiently. As a result, it is not necessary to perform complicated reaction operations and to use agents that are highly explosive. Accordingly, the target bipyridine compound can be synthesized with high purity and a high yield in a simple and safe manner in a short period of time.

Another feature is that a hydrogen donor is added to a reaction product produced through the reaction of the pyridine with the dispersion product obtained by dispersing an alkali metal in a dispersion solvent.

With this configuration, after the reaction of the pyridine with the dispersion product obtained by dispersing an alkali metal in a dispersion solvent, the hydrogen donor and the reaction product are reacted. Accordingly, the dimerization of the pyridine ring and the acceptance of hydrogen from the hydrogen donor can progress smoothly in succession, thus making it possible to synthesize the target bipyridine compound with high purity and a high yield.

Another feature is that the reaction solvent contains a hydrogen donor.

With this configuration, a combined solution is formed by adding the hydrogen donor to the reaction solvent, which is a reaction site in which the pyridine and the dispersion product obtained by dispersing an alkali metal in a dispersion solvent are reacted. Accordingly, it is not necessary to additionally perform a step of adding the hydrogen donor, thus making it possible to simplify the synthesis process. As a result, the target bipyridine compound can be synthesized in a simple manner through a small number of steps, thus making it possible to reduce production cost.

Another feature is that the bipyridine compound is any one of 2,2'-bipyridine, 4,4'-bipyridine, 2,4'-bipyridine, 2,3'-bipyridine, 3,3'-bipyridine, and 3,4'-bipyridine.

With this configuration, pyridine is used as a starting compound. Accordingly, 2,2'-bipyridine, 4,4'-bipyridine, 2,4'-bipyridine, 2,3'-bipyridine, 3,3'-bipyridine, or 3,4'-bipyridine, which is of particularly high utility value as a catalyst and an organic material, can be synthesized with high purity and a high yield in a simple and safe manner in a short period of time.

As a result of performing intensive studies to solve the above-mentioned problems, the inventors of the present invention also found that a target pyridine compound can be synthesized with high purity and a good yield by reacting a monomer with a dispersion product obtained by dispersing an alkali metal in a dispersion solvent without using a catalyst. In such a synthesis reaction, expensive agents are not needed, and the target pyridine compound can be synthesized in a simple manner in a short period of time through a small number of steps. Furthermore, it was found that when the pyridine compound synthesized with a high yield is dissolved in an organic solvent having a Hansen solubility parameter of 5 $JP^{1/2}/cm^{3/2}$ or more and 9 $J^{1/2}/cm^{3/2}$ or less for the pyridine compound, the pyridine compound can be efficiently recrystallized from the organic solvent. The inventors of the present invention achieved the present invention based on these findings.

Specifically, a method for manufacturing a pyridine compound includes a synthesis step of synthesizing a pyridine compound represented by General Formula (III) below by reacting, in a reaction solvent, a monomer with a dispersion product obtained by dispersing an alkali metal in a dispersion solvent, a deactivation step of deactivating the alkali metal remaining in a reaction solution containing the synthesized pyridine compound, a dissolving step of dissolving the pyridine compound by adding an organic solvent having a Hansen solubility parameter of 5 $J^{1/2}/cm^{3/2}$ or more and 9 $J^{1/2}/cm^{3/2}$ or less for the pyridine compound to the reaction solution in which the alkali metal has been deactivated, and a recrystallization step of recrystallizing the pyridine compound by cooling the organic solvent containing the pyridine compound.

Chemical Formula 3

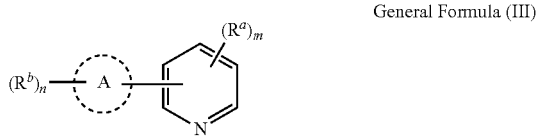

General Formula (III)

(In this formula, $R^a$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, A represents a hydrocarbon ring or a heterocyclic ring, $R^b$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, m represents 0 to 4, and when m is 2 to 4, $R^a$s are optionally the same or different, and n represents an integer of 0 or greater, and when n is an integer of 2 or greater, $R^b$s are optionally the same or different.)

In this method, the dispersion product obtained by dispersing an alkali metal in a dispersion solvent is used, thus making it possible to synthesize a pyridine compound at low cost with reduced man-hours without using an expensive palladium catalyst, unlike a conventional method. In addition, the pyridine compound can be synthesized with high purity and a good yield.

On the other hand, impurities such as the dispersion solvent are mixed in the reaction solution in which the alkali metal has been deactivated.

Using the organic solvent having a Hansen solubility parameter of 5 $J^{1/2}/cm^{3/2}$ or more and 9 $J^{1/2}/cm^{3/2}$ or less for the pyridine compound and performing cooling in the recrystallization step in the same manner as in this method make it easy to recrystallize only the pyridine compound from this organic solvent. The reason for this is that the pyridine compound can be easily dissolved in and isolated from the organic solvent having a Hansen solubility parameter within the above-mentioned range for the pyridine compound compared with alcohol having a high polarity. Distillation treatment is not required in this method, and therefore, the pyridine compound can be easily isolated without a large amount of labor. As a result, a manufacturing method according to which it is possible to synthesize a pyridine compound at low cost with reduced production man-hours and to collect the pyridine compound efficiently can be provided.

Another aspect of the manufacturing method further includes an evaporation step of evaporating the reaction solvent by heating the reaction solution in which the alkali metal has been deactivated, the evaporation step being performed prior to the dissolving step.

For example, the pyridine compound can be easily dissolved in an organic solvent such as tetrahydrofuran having a very small Hansen solubility parameter for the pyridine compound, but the solubility is excessively high, thus making it difficult to collect the pyridine compound from the reaction solvent in the recrystallization step. As a result, the collection yield decreases. However, evaporating the reaction solvent in advance in the same manner as in this aspect makes it possible to dissolve all the pyridine compound in an organic solvent having a Hansen solubility parameter of 5 $J^{1/2}/cm^{3/2}$ or more and 9 $J^{1/2}/cm^{3/2}$ or less for the pyridine compound in the dissolving step. Accordingly, the collection yield of the pyridine compound can be improved.

In another aspect of the manufacturing method, the reaction solvent evaporated in the evaporation step is cooled and reused as the reaction solvent in the synthesis step.

With this aspect, the reaction solvent used in the synthesis step is reused in the form of a liquid. As a result, the reaction solvent, a relatively large amount of which is required, can be prevented from being wastefully discarded, thus making it possible to reduce production cost.

Another aspect of the manufacturing method further includes a washing step of performing washing by adding water to a dissolution vessel used in the dissolving step, the washing step being performed prior to the dissolving step.

With this aspect, the pyridine compound and other impurities attaching to the dissolution vessel are washed with water, thus making it possible to recrystallize the synthesized pyridine compound efficiently.

In another aspect of the manufacturing method, the alkali metal is deactivated by adding water to the reaction solution in the deactivation step, a separation step of separating an organic layer containing the pyridine compound by filtering the reaction solution in which the alkali metal has been deactivated is performed after the deactivation step and prior to the dissolving step, and the pyridine compound is dissolved by adding the organic solvent to the organic layer in the dissolving step.

For example, tetrahydrofuran is used as the reaction solvent, the reaction solvent is dissolved in water. Therefore, in the separation step of this aspect, the organic layer containing the pyridine compound is separated in a state in which the reaction solvent is separated in the filtrate. As a result, a step of evaporating the reaction solvent, which adversely affects the collection of the pyridine compound, can be omitted, thus making it possible to simplify the manufacturing process.

In another aspect of the manufacturing method, the recrystallization step includes a concentration step of concentrating the organic solvent containing the pyridine compound by heating, a cooling step of cooling the organic solvent containing the pyridine compound, the cooling step being performed after the concentrating step, and a filtration step of filtering and collecting the pyridine compound, the filtration step being performed after the cooling step.

When concentration is performed by evaporating a suitable amount of the organic solvent in the same manner as in this aspect, the concentration of the pyridine compound is increased, thus making it possible to promote the recrystallization of the pyridine compound in the cooling step. Accordingly, the collection yield of the pyridine compound in the filtration step can be improved.

Another aspect of the manufacturing method further includes a second recrystallization step including: a second concentration step of concentrating, by heating, a filtrate produced in the filtration step in which the pyridine compound remains; a second cooling step of cooling the filtrate, the second cooling step being performed after the second concentration step; and a second filtration step of filtering and collecting the pyridine compound, the second filtration step being performed after the second cooling step.

The pyridine compound that has not been recrystallized in the cooling step may remain in the filtrate produced in the filtration step. Collecting the pyridine compound again from the filtrate produced in the recrystallization step in the same manner as in this aspect makes it possible to further improve the collection yield of the pyridine compound.

In another aspect of the manufacturing method, the pyridine compound collected in the second filtration step is mixed in the organic solvent used in the recrystallization step.

Since the organic solvent is concentrated again in the second concentration step, insulating oil or the like serving as the dispersion solvent for an alkali metal may attach to the surface of the pyridine compound. Mixing the pyridine compound collected in the second filtration step again in the organic solvent used in the first recrystallization step in the same manner as in this aspect makes it possible to separate the insulating oil from the pyridine compound. Accordingly, the purity of the pyridine compound can be further improved.

BRIEF DESCRIPTION OF DRAWINGS

FIG. 1 is a diagram summarizing the synthesis conditions and the synthesis results in Example 1 in which the synthesis of 4,4'-di-tert-butyl-2,2'-bipyridine is investigated.

FIG. 2 is a diagram summarizing the synthesis conditions and the synthesis results in Example 2 in which the synthesis of 4,4'-di-tert-butyl-2,2'-bipyridine is investigated.

DESCRIPTION OF EMBODIMENTS

Hereinafter, embodiments of a method of synthesizing a bipyridine compound and a method of manufacturing a pyridine compound according to the present invention will be described in detail. However, the present invention is not limited to the embodiments described below.

[Synthesis of Pyridine Compound]

Figure 6:
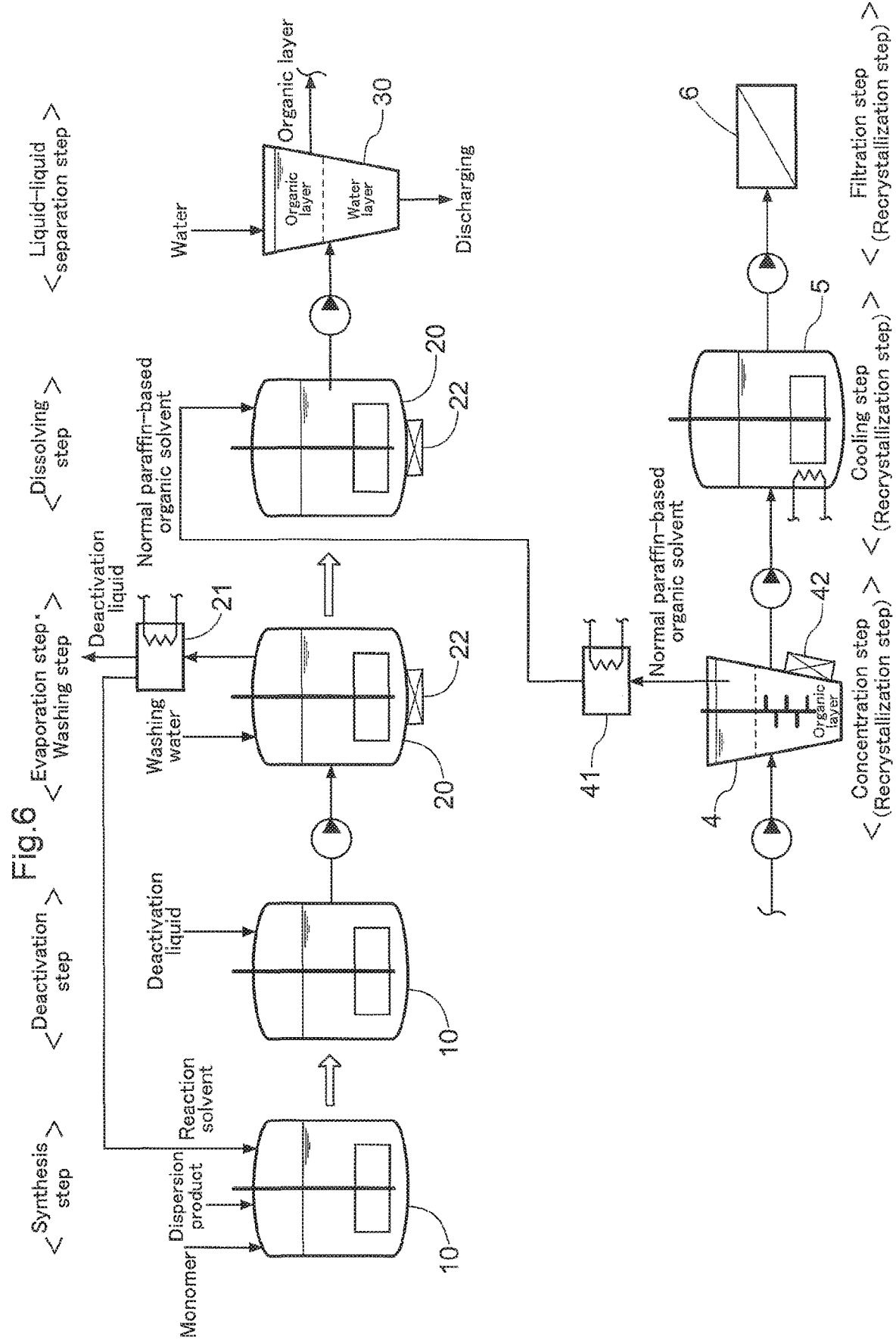
FIG. 6 is a flowchart illustrating a method for manufacturing a pyridine compound.

As shown in FIG. 6, a method for manufacturing a pyridine compound according to this embodiment includes a synthesis step of synthesizing a pyridine compound represented by General Formula (I) below by reacting, in a reaction solvent, a monomer with a dispersion product obtained by dispersing an alkali metal in a dispersion solvent, and a deactivation step of deactivating the alkali metal remaining in a reaction solution containing the synthesized pyridine compound. The synthesis step and the deactivation step are carried out under stirring in the same reaction vessel 10. It should be noted that the synthesis step and the deactivation step may be carried out in separate vessels or in the reaction vessel 10 without stirring, and there is no particular limitation thereto.

A pyridine compound is a compound including an optionally substituted pyridine ring in which an optionally substituted hydrocarbon ring or an optionally substituted heterocyclic ring that is separate from the pyridine ring is linked to the pyridine ring. The pyridine ring and the hydrocarbon ring or heterocyclic ring may be linked to each other at any position as long as carbon in the pyridine ring and carbon in the hydrocarbon ring or heterocyclic ring are linked through a carbon-carbon bond. Specifically, the pyridine compound is a compound represented by General Formula (I) below.

Chemical Formula 4

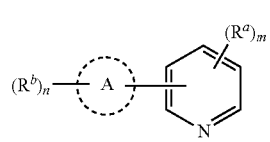

General Formula (I)

(In this formula, $R^a$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, A represents a hydrocarbon ring or a heterocyclic ring, $R^b$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, m represents 0 to 4, and when m is 2 to 4, $R^a$s are optionally the same or different, and n represents an integer of 0 or greater, and when n is an integer of 2 or greater, $R^b$s are optionally the same or different.)

$R^a$ is an atom or an atomic group that is introduced so as to be substituted for a hydrogen atom in the pyridine ring. $R^a$ may be introduced into any position in the pyridine ring, and may be introduced into a plurality of positions. $R^a$ is introduced into a position of carbon linked to a hydrogen atom in the pyridine ring, and up to four $R^a$s can be introduced. When introduced into a plurality of positions, $R^a$s may be the same or different. $R^a$ need not be introduced. For example, $R^a$ is an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group. In this case, examples of a substituent include a halogen atom, a hydroxy group, an aldehyde group, a carboxyl group, an amino group, and a cyano group. $R^a$ is preferably a lower alkyl group. The alkyl group may be a linear or branched alkyl group. A t-butyl group is particularly preferable.

A is a hydrocarbon ring or a heterocyclic ring, and preferably an aromatic ring. Examples of the hydrocarbon ring include a benzene ring, a naphthalene ring, and an anthracene ring. Examples of the heterocyclic ring include: nitrogen-containing heterocyclic rings such as a pyridine ring, a pyrazine ring, a pyrimidine ring, a pyrrole ring, and a pyrazole ring; sulfur-containing heterocyclic rings such as a thiophene ring; and oxygen-containing heterocyclic ring such as a furan ring. A benzene ring or a pyridine ring is preferable.

$R^b$ is an atom or an atomic group that is introduced so as to be substituted for a hydrogen atom that is linked to carbon in the hydrocarbon ring or heterocyclic ring represented by A. $R^b$ may be introduced into any position in A, and may be introduced into a plurality of positions. $R^b$ is introduced into a position of carbon linked to a hydrogen atom in the hydrocarbon ring or heterocyclic ring represented by A, and the maximum number of $R^b$s that can be introduced is equal to the number of hydrogen atoms linked to the carbon. When introduced into a plurality of positions, $R^b$s may be the same or different. $R^b$ need not be introduced. For example, $R^b$ is an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group. In this case, examples of a substituent include a halogen atom, a hydroxy group, an aldehyde group, a carboxyl group, an amino group, and a cyano group. $R^b$ is preferably a lower alkyl group. The alkyl group may be a linear or branched alkyl group. A t-butyl group is particularly preferable.

Preferable examples of the pyridine compound includes di-tert-butyl-2,2'-bipyridine compounds, and 4,4'-di-tert-butyl-2,2'-bipyridine is particularly preferable. In addition, bipyridine compounds such as dimethyl-2,2'-bipyridine, 2,2'-bipyridine, 4,4'-bipyridine, 2,4'-bipyridine, 2,3'-bipyridine, 3,3'-bipyridine, and 3,4'-bipyridine are also preferable.

In this specification, a combination of a compound including an optionally substituted pyridine ring and a compound including an optionally substituted hydrocarbon ring or an optionally substituted heterocyclic ring is used as a monomer serving as a starting material.

The compound including an optionally substituted pyridine ring is represented by General Formula (II) or (III) below.

Chemical Formula 5

General Formula (II)

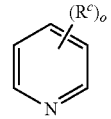

(In this formula, $R^c$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, o represents 0 to 4, and when o is 2 to 4, $R^c$s may be the same or different.)

Chemical Formula 6

General Formula (III)

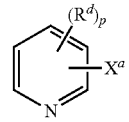

(In this formula, $R^d$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, $X^a$ represents a halogen atom, p represents 0 to 4, and when p is 2 to 4, $R^d$s may be the same or different.)

$R^c$ and $R^d$ correspond to $R^a$ in the pyridine compound. $X^a$ is a halogen atom such as a fluorine atom, a chlorine atom, a bromine atom, or an iodine atom. In the synthesis reaction of the pyridine compound, $X^a$ is substituted by the compound including an optionally substituted hydrocarbon ring or an optionally substituted heterocyclic ring.

The compound including an optionally substituted pyridine ring is preferably a tert-butylpyridine compound, a halogenated methylpyridine compound, or a mixture of a halogenated methylpyridine compound and a halogenated benzene compound, and particularly preferably 4-tert-butylpyridine. In addition, non-substituted pyridine can be preferably used.

The compound including an optionally substituted hydrocarbon ring or an optionally substituted heterocyclic ring is represented by General Formula (IV) or (V) below.

Chemical Formula 7

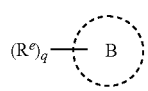

General Formula (IV)

(In this formula, B represents a hydrocarbon ring or a heterocyclic ring, $R^e$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, q represents an integer of 0 or greater, and when q is an integer of 2 or greater, $R^c$s may be the same or different.)

Chemical Formula 8

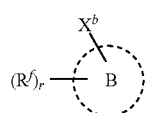

General Formula (V)

(In this formula, B represents a hydrocarbon ring or a heterocyclic ring, $R^f$ represents an optionally substituted alkyl group, an optionally substituted alkenyl group, an optionally substituted alkynyl group, an optionally substituted aryl group, an optionally substituted arylalkyl group, an optionally substituted alkoxy group, an optionally substituted acyl group, an optionally substituted amino group, an optionally substituted alkylthio group, an optionally substituted arylthio group, an optionally substituted arylalkylthio group, a halogen atom, a hydroxy group, an aldehyde group, a carboxyl group, an amino group, or a cyano group, $X^b$ represents a halogen atom, r represents an integer of 0 or greater, and when r is an integer of 2 or greater, $R^f$s may be the same or different.)

B corresponds to A in the pyridine compound, and $R^e$ and $R^f$ correspond to $R^b$ in the pyridine compound. $X^b$ is a halogen atom such as a fluorine atom, a chlorine atom, a bromine atom, or an iodine atom. In the synthesis reaction of the pyridine compound, $X^b$ is substituted by an optionally substituted pyridine ring.

The compound including an optionally substituted hydrocarbon ring or an optionally substituted heterocyclic ring is preferably a tert-butylpyridine compound, a halogenated methylpyridine compound, or a mixture of a halogenated methylpyridine compound and a halogenated benzene compound, and non-substituted pyridine can be preferably used. In particular, 4-tert-butylpyridine, pyridine, 2-chloro-4-methylpyridine, or a mixture of 2-chloro-4-methylpyridine and halogenated benzene is preferably used. In addition, non-substituted pyridine can be preferably used.

It should be noted that if the monomer includes a highly reactive functional group, it is preferable to protect this functional group with a suitable protecting group during the synthesis reaction of the pyridine compound, and the protected functional group is deprotected using a suitable means after the reaction finishes.

The dispersion product obtained by dispersing an alkali metal in a dispersion solvent is a dispersion product obtained by dispersing minute particles of an alkali metal in an antisolvent, or a dispersion product obtained by dispersing an alkali metal in a liquid form in an antisolvent. Examples of the alkali metal include sodium, potassium, lithium and alloys thereof. The average particle diameter of the minute particles is preferably less than 10 µm, and the minute particles having an average particle diameter of less than 5 µm can be used particularly preferably. The diameter of a sphere having a projected area equal to the projected area obtained through image analyses of photomicrographs is taken as the average particle diameter.

A solvent known in the art can be used as the dispersion solvent as long as minute particles of an alkali metal or an alkali metal in a liquid form can be dispersed in an antisolvent, and the reaction of the monomer with the dispersion product of the alkali metal is not inhibited. Examples thereof include aromatic solvents such as xylene and toluene, normal paraffin-based solvents such as decane, and mixed solvents thereof.

Hereinafter, the dispersion product obtained by dispersing an alkali metal in a dispersion solvent may be abbreviated as "SD". SD is an abbreviation of "sodium dispersion". In Examples described below, sodium is used as the alkali metal, and therefore, the dispersion product is denoted by the abbreviation "SD". However, alkali metals other than sodium are also encompassed by the abbreviation "SD".

A solvent known in the art can be used as the reaction solvent as long as the reaction of the monomer with SD is not inhibited. Examples thereof include ether-based solvents, normal paraffin-based solvents, aromatic solvents, amine-based solvents, and heterocyclic compound solvents. As the ether-based solvent, a cyclic ether solvent is preferable, and tetrahydrofuran (which may be abbreviated as "THF" hereinafter) is particularly preferable. As the normal paraffin-based solvent, normal decane or the like is particularly preferable. As the aromatic solvent, xylene, toluene, or the like can be preferably used, and as the amine-based solvent, ethylene diamine or the like can be preferably used. As the heterocyclic compound solvent, tetrahydrothiophene or the like can be used. In addition, mixed solvents thereof can also be used. In this specification, the above-described dispersion solvent and the reaction solvent may be the same or different.

Alcohol or water is used as a deactivation liquid used in the deactivation step of deactivating the alkali metal remaining after the reaction. Lower alcohol such as isopropyl alcohol, methanol, or ethanol is preferably used as the alcohol, but higher alcohol may also be used, and there is no particular limitation thereto. On the other hand, when water is used, it is preferable to perform the deactivation step in an atmosphere of inert gas that is filled with argon gas, nitrogen gas, or the like. It should be noted that when SD is used in the synthesis of the pyridine compound, sodium is hydrogenated and is stable, and therefore, the deactivation step may be carried out in an atmosphere of air when water is used. When alcohol is used, the deactivation step may be carried out in an atmosphere of inert gas, and there is no particular limitation thereto.

Hereinafter, as an example of a method for synthesizing a bipyridine compound, the synthesis of a di-tert-butyl-2,2'-bipyridine compound represented by General Formula (VI) below will be described.

Chemical Formula 9

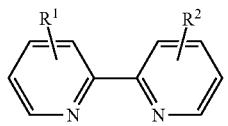

General Formula (VI)

(In this formula, $R^1$ and $R^2$ are independently tert-butyl groups. $R^1$ is introduced into any one of 1-position, 2-position, 3-position, and 4-position, and hydrogen groups are introduced into the other positions. $R^2$ is introduced into any one of 1'-position, 2'-position, 3'-position, and 4'-position, and hydrogen groups are introduced into the other positions.)

A reaction product a represented by General Formula (VII) below is obtained by reacting tert-butylpyridine compound with SD in the reaction solvent. Then, hydrogen is provided to the reaction product a represented by General Formula (VII) below by reacting the reaction product a with a hydrogen donor, and a reaction product b represented by General Formula (VIII) below is thus obtained. The target di-tert-butyl-2,2'-bipyridine compound is synthesized by oxidizing the reaction product b with air.

Chemical Formula 10

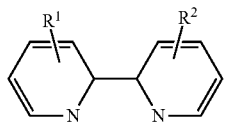

General Formula (VII)

Chemical Formula 11

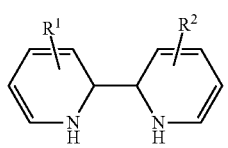

General Formula (VIII)

(In General Formulae (VII) and (VIII), $R^1$ and $R^2$ are independently tert-butyl groups. $R^1$ is introduced into any one of 1-position, 2-position, 3-position, and 4-position, and hydrogen groups are introduced into the other positions. $R^2$ is introduced into any one of 1'-position, 2'-position, 3'-position, and 4'-position, and hydrogen groups are introduced into the other positions.)

With the method for synthesizing a di-tert-butyl-2,2'-bipyridine compound according to this embodiment, the dispersion product obtained by dispersing an alkali metal in a dispersion solvent is used, and the pyridine ring dimerization reaction can progress smoothly and efficiently. It is not necessary to perform complicated reaction operations and to use agents that are highly explosive, and the di-tert-butyl-2,2'-bipyridine compound can be synthesized with high purity and a high yield in a simple and safe manner in a short period of time.

2-tert-Butylpyridine, 3-tert-butylpyridine, or 4-tert-butylpyridine can be used as the tert-butylpyridine compound. 4-tert-Butylpyridine is preferable. These tert-butylpyridine compounds may be commercially available tert-butylpyridine compounds or tert-butylpyridine compounds manufactured in accordance with a method known in the art.

A substance known in the art can be used as the hydrogen donor as long as the substance provides, through an oxidation-reduction reaction, hydrogen to the reaction product a represented by General Formula (VII), which is formed through the reaction of a tert-butylpyridine compound with SD, and the substance itself is dehydrogenated. Water or alcohol can be used, for example. Lower alcohol having about 1 to 6 carbon atoms can be preferably used, and an example thereof is tert-butanol.

(Details of Synthesis Process)

Hereinafter, the synthesis process of the di-tert-butyl-2,2'-bipyridine compound according to this embodiment will be described in detail. First, the reaction product a represented by General Formula (VII) is obtained by reacting, in the reaction solvent, a tert-butylpyridine compound with the dispersion product obtained by an alkali metal in a dispersion solvent. There is no particular limitation on the reaction temperature in this reaction. The reaction can be performed at room temperature, and preferably at 25 to 50° C. Therefore, it is not necessary to provide a temperature controlling means for heating, cooling, and the like. It should be noted that a temperature controlling means may also be provided as necessary, and there is no particular limitation thereto.

There is also no particular limitation on the reaction time, and it is sufficient that the reaction time is set as appropriate depending on the reaction temperature, and the types and amounts of the reaction agents. In general, the reaction time is 1 to 24 hours, and preferably 1 to 6 hours. Even if the reaction time is extended, the yield of the target di-tert-butyl2,2'-bipyridine compound does not increase, and the recovery rate of the tert-butylpyridine compound, which is a raw material, decreases, resulting in the deterioration of the material balance. Therefore, a long-term reaction is not preferable from the viewpoint of the yield and the reuse of the raw material.

Next, hydrogen is provided to the reaction product a represented by General Formula (VII) by reacting the reaction product a with a hydrogen donor, and a reaction product b represented by General Formula (VIII) is thus obtained. It is preferable to perform the reaction with the hydrogen donor in an atmosphere of inert gas (e.g., in a reaction vessel or the like that is filled with argon gas, nitrogen gas, or the like).

In the reaction with the hydrogen donor, the hydrogen donor may be reacted with a reaction mixture of the reaction product a represented by General Formula (VII) and SD without isolating the reaction product a after the reaction of the tert-butylpyridine compound with SD, or the hydrogen donor may be reacted with the reaction product a represented by General Formula (VII) after an operation such as isolation, extraction, or concentration is performed on the reaction product a. Therefore, a combined solution may be prepared by adding the hydrogen donor to the solvent in advance prior to the reaction of the tert-butylpyridine compound with SD, and the hydrogen donor can also be added during the reaction with SD or after the reaction with SD. It should be noted that the hydrogen donor may be added at timings combined as appropriate, such as setting the timings to be both before and after the reaction of the tert-butylpyridine compound with SD.

When the hydrogen donor is added to the solvent in advance, it is not necessary to additionally perform a step of adding the hydrogen donor, thus making it possible to further simplify the synthesis process and reduce production cost. On the other hand, reacting the hydrogen donor with the produced reaction product a represented by General Formula (VII) after the reaction with SD is advantageous in that the dimerization of the pyridine ring and the acceptance of hydrogen from the hydrogen donor can progress smoothly in succession, thus making it possible to synthesize the target di-tert-butyl-2,2'-bipyridine compound with high purity and a high yield.

Lastly, the target di-tert-butyl-2,2'-bipyridine compound is obtained by oxidizing the reaction product b represented by General Formula (VIII). This oxidation reaction is performed using a method known in the art. Examples thereof include air oxidation and an oxidizing agent. It is preferable to perform the oxidation through air oxidation in a state in which the reaction vessel 10 is open to the atmosphere.

In this specification, in the reaction of the tert-butylpyridine compound with SD, the tert-butylpyridine compound is reacted with SD in an amount of 1 mol equivalent or more and 2.5 mol equivalent or less, preferably 1 mol equivalent or more and 2 mol equivalent or less, and particularly preferably 1 mol equivalent, with respect to the tert-butylpyridine compound, in THF preferably in an amount of 1 ml or more and 4 ml or less, particularly preferably 2 ml, with respect to 0.5 mmol of the tert-butylpyridine. That is, it is preferable that the usage amount of the solvent is 2 ml or more and 8 ml or less, and particularly preferably 4 ml, with respect to 1 mmol of the tert-butylpyridine compound. "Molar equivalent with respect to the tert-butylpyridine compound" herein means the substance amount ratio in terms of the alkali metal contained in SD with respect to the tert-butylpyridine compound added to the reaction system. When a solvent other than THF is used as the reaction solvent, the usage amounts of the solvent and SD can also be optimized.

Optimizing the usage amounts of the solvent and SD in this manner causes the reaction to progress smoothly, thus making it possible to suppress the generation of reaction by-products and to synthesize the target di-tert-butyl-2,2'-bipyridine compound with high purity and a high yield. In addition, the raw materials can be used in the correct amounts in the synthesis, thus making it possible to synthesize the target di-tert-butyl-2,2'-bipyridine compound with a favorable material balance.

The obtained di-tert-butyl-2,2'-bipyridine compound may be purified using a purification means known in the art, such as column chromatography, distillation, or recrystallization. A configuration may be adopted in which the residual unreacted tert-butylpyridine compound is recovered and reused in the synthesis of the di-tert-butyl-2,2'-bipyridine compound.

The di-tert-butyl-2,2'-bipyridine compound obtained in this manner is preferably 3,3'-di-tert-butyl-2,2'-bipyridine, 4,4'-di-tert-butyl-2,2'-bipyridine, or 5,5'-di-tert-butyl-2,2'-bipyridine, and particularly preferably 4,4'-di-tert-butyl-2,2'-bipyridine.

Hereinafter, the synthesis of 4,4'-di-tert-butyl-2,2'-bipyridine will be shown as an example and described more specifically, but there is no limitation thereto.

Reaction Scheme (I) below shows the synthesis scheme of 4,4'-di-tert-butyl-2,2'-bipyridine. In this reaction, THF is used as the reaction solvent, and a dispersion product of sodium metal is used as SD.

Reaction scheme (I)

Chemical Formula 12

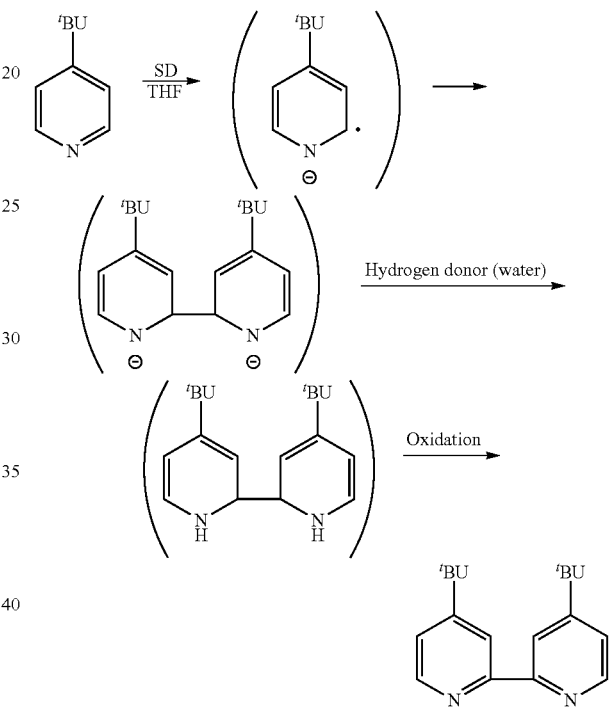

When a 4-tert-butylpyridine compound, which is a starting material, is reacted with SD in THF, an electron is released from the sodium metal. The electron released from the sodium metal enters the pyridine ring, and a radical anion is thus generated. The pyridine rings are linked to each other through a coupling reaction of the radical anions, and a bipyridine ring is thus generated. Then, nitrogen atoms in the bipyridine ring receive hydrogen from the hydrogen donor, and 4,4'-di-tert-butyl-1,1',2,2'-tetrahydro-2,2'-bipyridine is thus generated. The target 4,4'-di-tert-butyl-2,2'-bipyridine compound is obtained by oxidizing 4,4'-di-tert-butyl-1,1',2,2'-tetrahydro-2,2'-bipyridine. It is sufficient that 4,4'-di-tert-butyl-1,1',2,2'-tetrahydro-2,2'-bipyridine is oxidized using pure oxygen, gas containing oxygen such as air, or ozone. The oxidation may also be performed using an oxidizing agent such as nitric acid.

Another Embodiment

A method for synthesizing a bipyridine compound of another embodiment is a method for synthesizing a bipyridine compound represented by General Formula (IX) below.

Chemical Formula 13

General Formula (IX)

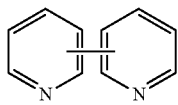

The method for synthesizing a bipyridine compound of another embodiment includes a step of reacting pyridine ($C_5H_5N$) with SD in the reaction solvent. This method can be performed in the same manner as the above-described method for synthesizing a di-tert-butyl-2,2'-bipyridine compound, and details of the synthesis are as described above. Also in the reaction with the hydrogen donor, the hydrogen donor may be reacted with a reaction mixture of SD and the reaction product generated through the reaction of pyridine with SD without isolating the reaction product, or the hydrogen donor may be reacted with the reaction product after an operation such as isolation, extraction, or concentration is performed on the reaction product. Therefore, a combined solution may be prepared by adding the hydrogen donor to the solvent in advance prior to the reaction of the tert-butylpyridine compound with SD, and the hydrogen donor can also be added during the reaction with SD or after the reaction with SD. The oxidation of the reaction product after the reaction with the hydrogen donor can also be performed as described above.

The obtained bipyridine compound may be purified using a purification means known in the art, such as column chromatography, distillation, or recrystallization. A configuration may be adopted in which the residual unreacted pyridine is recovered and reused in the synthesis of the bipyridine compound.

The bipyridine compound obtained in this manner is not substituted, and is preferably 2,2'-bipyridine, 4,4'-bipyridine, 2,4'-bipyridine, 2,3'-bipyridine, 3,3'-bipyridine, or 3,4'-bipyridine. 4,4'-Bipyridine is particularly preferable.

(Synthesis of Bipyridine Compound Having Another Substituent)

Applying the method for synthesizing a di-tert-butyl-2,2'-bipyridine compound of the above-described embodiment to the synthesis of a di-tert-butyl-2,2'-bipyridine compound using tert-butylpyridine as a substrate for the synthesis makes it possible to synthesize a target bipyridine compound with high purity and a high yield. Moreover, the method for synthesizing a bipyridine compound of another embodiment is applied to the synthesis of a bipyridine compound that is not substituted using bipyridine that is not substituted as a substrate for the synthesis. Therefore, it is not preferable to apply this method to the synthesis using a pyridine compound having a substituent other than a tert-butyl group as a substrate for the synthesis. For example, when a bipyridine compound is synthesized using, as a substrate, a pyridine compound or the like having a methyl group, a phenyl group, a dimethylamino group, or the like as a substituent, a target bipyridine compound cannot be synthesized with high purity and a high yield as achieved in the synthesis of the di-tert-butyl-2,2'-bipyridine compound.

EXAMPLES

This embodiment will be described in detail by way of the following examples. In the following examples, a method for synthesizing 4,4'-di-tert-butyl-2,2'-bipyridine that uses 4-tert-butylpyridine as the starting material, a dispersion product obtained by dispersing minute particles of sodium metal in an antisolvent as SD, and THF as the reaction solvent is shown as an example of the method for synthesizing a di-tert-butyl-2,2'-bipyridine compound, but there is no limitation thereto.

Example 1: Investigation of Synthesis of 4,4'-di-tert-butyl-2,2'-bipyridine-1

In this example, the synthesis of 4,4'-di-tert-butyl-2,2'-bipyridine was investigated.

4-tert-Butylpyridine (0.5 mmol) was reacted with SD in an amount of molar equivalents with respect to 4-tert-butylpyridine as shown in FIG. 1 in 1 ml of THF. The reaction temperatures and the reaction times were set as shown in FIG. 1. A dispersion product obtained by dispersing sodium in normal paraffin oil was used as SD. "Molar equivalent with respect to 4-tert-butylpyridine" means the substance amount ratio in terms of sodium metal contained in SD. Next, a large amount of water was added as the hydrogen donor to provide hydrogen to the product obtained through the reaction of 4-tert-butylpyridine with SD and to deactivate the sodium metal in SD while suppressing the generation of heat. After the deactivation of the sodium metal, the target product 4,4'-di-tert-butyl-2,2'-bipyridine was obtained through air oxidation.

After the reaction, the amount of the produced target reaction product 4,4'-di-tert-butyl-2,2'-bipyridine (Compound 2) was measured using $^1H$ NMR, and the yield was calculated based on the amount of 4-tert-butylpyridine added to the reaction system. At the same time, the yields of 4-tert-butyl-1,4-dihydropyridine (Compound 1) and 4,4',4"-tri-tert-butyl-2,2':6',2"-terpyridine (Compound 3), which are possible reaction by-products, were calculated in the same manner.

Here, the "yield" means the ratio of the amount of actually obtained 4,4'-di-tert-butyl-2,2'-bipyridine to the amount of 4,4'-di-tert-butyl-2,2'-bipyridine that can be theoretically produced using the maximum amount of 4-tert-butylpyridine added to the reaction system. 4,4'-di-tert-Butyl-2,2'-bipyridine is a dimer of 4-tert-butylpyridine, and therefore, if 0.25 mmol of 4,4'-di-tert-butyl-2,2'-bipyridine is obtained from 0.5 mmol of 4-tert-butylpyridine, the yield is 100%.

In addition, the amount of unreacted 4-tert-butylpyridine remaining in the reaction system was measured, and the ratio of the unreacted 4-tert-butylpyridine to the amount of 4-tert-butylpyridine added to the reaction system was taken as a recovery rate.

The results are summarized in FIG. 1. It is found from these results that when 4-tert-butylpyridine (0.5 mmol) was reacted with SD in an amount of 1 to 2.5 mol equivalents with respect to the 4-tert-butylpyridine in 1 ml of THF at 25 to 50° C. for 2 to 6 hours, the yield of 4,4'-di-tert-butyl-2,2'-bipyridine was about 50%. In particular, when 4-tert-butylpyridine was reacted with SD in an amount of 2.5 mol equivalents with respect to the 4-tert-butylpyridine for 2 hours, and 4-tert-butylpyridine was reacted with SD in an amount of 1 mol equivalent with respect to the 4-tert-butylpyridine for 2 and 6 hours, 4,4'-di-tert-butyl-2,2'-bipyridine could be obtained with a good yield. In particular, when 4-tert-butylpyridine was reacted with SD in an amount of 1 mol equivalent with respect to the 4-tert-butylpyridine at 25° C. for 2 hours, Compounds 1 and 3, which are reaction by-products, were not synthesized, and the 4,4'-di-tert-butyl-2,2'-bipyridine compound was obtained with high purity and a high yield. In addition, the material balance was also favorable.

On the other hand, when the reaction temperature was set to 0° C., a large amount of 4-tert-butylpyridine remained unreacted, but Compounds 1 and 3, which are reaction by-products, were not synthesized, and the 4,4'-di-tert-butyl-2,2'-bipyridine compound was obtained with high purity.

Example 2: Investigation of Synthesis of 4,4'-di-tert-butyl-2,2'-bipyridine-2

In this example, following Example 1, the synthesis of 4,4'-di-tert-butyl-2,2'-bipyridine was investigated. In this example, the synthesis was performed through the reaction of 4-tert-butylpyridine with SD at low concentrations in THF.

4-tert-Butylpyridine (0.5 mmol) was reacted with SD in an amount of molar equivalents with respect to 4-tert-butylpyridine as shown in FIG. 2 in THF. The usage amounts of THF, the reaction temperatures and the reaction times were set as shown in FIG. 2, and the synthesis was performed in the same manner as in Example 1.

After the reaction, in the same manner as in Example 1, the production amounts of 4,4'-di-tert-butyl2,2'-bipyridine (Compound 2), which was the target reaction product, and 4-tert-butyl-1,4-dihydropyridine (Compound 1) and 4,4',4"-tri-tert-butyl-2,2':6',2"-terpyridine (Compound 3), which were the possible reaction by-products, were measured, and their yields were calculated. The recovery rate of the unreacted 4-tert-butylpyridine was calculated in the same manner.

The results are summarized in FIG. 2. It is found from these results that when 4-tert-butylpyridine (0.5 mmol) was reacted with SD in an amount of 1 to 2 mol equivalents with respect to the 4-tert-butylpyridine in 2 to 4 ml of THF at 25 to 50° C. for 1 to 24 hours, the 4,4'-di-tert-butyl-2,2'-bipyridine compound was obtained with a high yield in all of the cases. In particular, when 0.5 mmol 4-tert-butylpyridine was reacted with SD in an amount of 1 mol equivalent with respect to the 4-tert-butylpyridine in 2 ml of THF at 50° C. for 1 to 6 hours, the 4,4'-di-tert-butyl-2,2'-bipyridine compound was obtained with a high yield without the generation of reaction by-products. In addition, when 0.5 mmol 4-tert-butylpyridine was reacted with SD in an amount of 1 mol equivalent with respect to the 4-tert-butylpyridine in 4 ml of THF at 25° C. for 6 hours, the 4,4'-di-tert-butyl-2,2'-bipyridine compound was obtained with a high yield without the generation of reaction by-products. It was found that when SD in an amount of 2 mol equivalents was used, the yield decreased compared with the case of 1 mol equivalent, and the material balance also decreased. It was also found from comparison with Example 1 that the lower the concentrations of 4-tert-butylpyridine and SD were with respect to THF, the higher the yield was.

Example 3: Investigation of Synthesis of 4,4'-di-tert-butyl-2,2'-bipyridine-3

In this example, the synthesis of 4,4'-di-tert-butyl-2,2'-bipyridine was investigated. In this example, the synthesis was performed in a state in which the hydrogen donor had been added to the reaction solvent.

Figure 3:
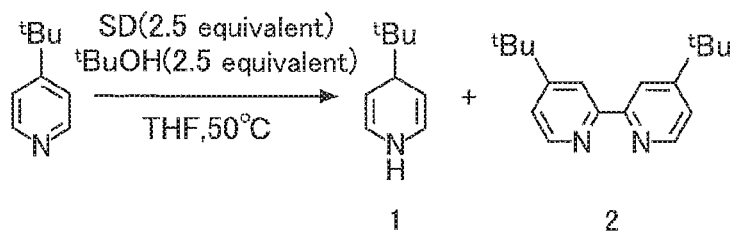
FIG. 3 is a diagram summarizing the synthesis conditions and the synthesis results in Example 3 in which the synthesis of 4,4'-di-tert-butyl-2,2'-bipyridine is investigated.

0.5 mmol of 4-tert-butylpyridine was reacted with SD in an amount of 2.5 mol equivalents with respect to 4-tert-butylpyridine as shown in FIG. 3 in 1 ml of THF containing tert-butanol in an amount of 2.5 mol equivalents at 50° C. Reaction times were set as shown in FIG. 3. The synthesis was performed in the same manner as in Example 1, except that the hydrogen donor had been added to the reaction solvent.

After the reaction, in the same manner as in Example 1, the production amounts of 4,4'-di-tert-butyl2,2'-bipyridine (Compound 2), which was the target reaction product, and 4-tert-butyl-1,4-dihydropyridine (Compound 1), which was the possible reaction by-product, were measured, and their yields were calculated. The recovery rate of the unreacted 4-tert-butylpyridine was calculated in the same manner.

The results are summarized in FIG. 3. It is found from these results that the 4,4'-di-tert-butyl-2,2'-bipyridine compound was obtained even in the presence of tert-butanol serving as the hydrogen donor. The yield also increased due to the reaction time being set to 2 hours. However, it was found that the yield and the material balance decreased compared with Examples 1 and 2 in which the hydrogen donor was added after the reaction with SD. It can be understood from these results that it is more preferable to perform the reaction with the hydrogen donor after the reaction with SD from the viewpoint of the yield.

Example 4: Investigation of Substrate Applicability

In this example, pyridine compounds having a substituent other than a tert-butyl group were used as the substrate of the synthesis of a bipyridine compound to investigate whether or not the bipyridine compound was synthesized with high purity and a high yield similarly to Examples 1 to 3.

In this example, 4-methylpyridine, which is a methyl-group substitution product of pyridine, 4-phenylpyridine, which is a phenyl-group substitution product of pyridine, and 4-dimethylaminopyridine, which is a dimethylamino-group substitution product, were used as the pyridine compounds, and the synthesis of bipyridine compounds was investigated. Specifically, 0.5 mmol of each substrate was reacted with SD in an amount of 1 mol equivalent with respect to the substrate in 1 or 2 ml of THF. The reaction temperatures and the reaction times were set as shown in FIG. 4, and the synthesis was performed in the same manner as in Example 1.

Regarding each substrate, after the reaction, the production amounts of the bipyridine compound (Compound 2), which was the target reaction product, and the reaction by-product (Compound 1) were measured, and their yields were calculated. The recovery rates of the unreacted substrates were calculated in the same manner.

Figure 4:
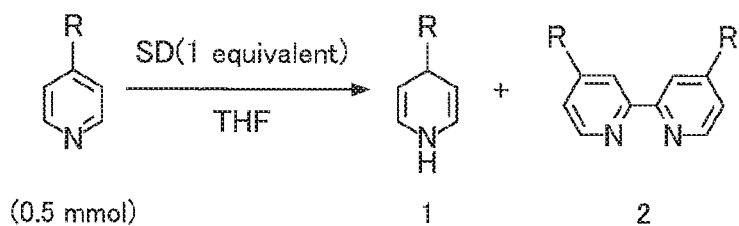
FIG. 4 is a diagram summarizing the synthesis conditions and the synthesis results in Example 4 in which substrate applicability is investigated.

The results were summarized in FIG. 4. It was found from these results that in all the cases where these substrates were used, the target bipyridine compounds were not obtained, or the yields were very low if the target bipyridine compounds were obtained. In particular, when 4-methylpyridine was used, the recovery rates of the substrates were low, and the material balance was problematic. It can be said from these results that with the synthesis methods of Examples 1 to 3, the di-tert-butyl2,2'-bipyridine compounds were synthesized with good purity and good yields.

Example 5: Investigation of Synthesis of 4,4-bipyridine

In this example, pyridine having no substituents was used as the substrate in the synthesis of a bipyridine compound to investigate the synthesis of a bipyridine compound.

Specifically, 1 mmol of pyridine was reacted with SD (2 mmol) in an amount of 2 mol equivalents with respect to pyridine in 1 ml of a reaction solvent (THF:EDA=1:1). The reaction temperature was set to 25° C., and the reaction time was set to 3 hours.

After the reaction, the amount of the reaction product was measured using GC/MS, and the ratio in percentage (%) thereof to all the products was calculated as the presence ratio (%) of the reaction product.

Figure 5:
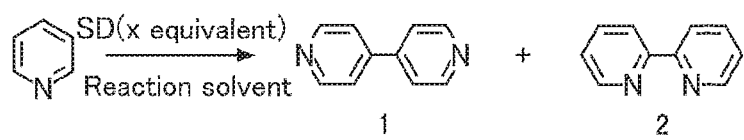
FIG. 5 is a diagram summarizing the synthesis conditions and the synthesis results in Example 5 in which the synthesis of 4,4'-bipyridine is investigated.

The results were summarized in FIG. 5. It was found from these results that when pyridine having no substituents was used as the substrate, 4,4'-bipyridine was obtained as the main product. 2,2'-Bipyridine was obtained as the by-product.

[Purification of Pyridine Compound]

As shown in FIG. 6, the method for manufacturing a pyridine compound according to this embodiment further includes a dissolving step of dissolving the pyridine compound by adding an organic solvent having a Hansen solubility parameter $\delta$ of 5 $J^{1/2}/cm^{3/2}$ or more and 9 $J^{1/2}/cm^{3/2}$ or less for the pyridine compound to the reaction solution in which the alkali metal has been deactivated, and a recrystallization step of recrystallizing the pyridine compound by cooling the organic solvent containing the pyridine compound.

Here, the "Hansen solubility parameter $\delta$" for the pyridine compound means a solubility parameter between the pyridine compound and the organic solvent calculated using Equation (1). The Hansen solubility parameter $\delta$ refers to a solubility of the pyridine compound, and the smaller the value is, the easier the pyridine compound dissolves in an organic solvent. When the Hansen solubility parameter $\delta$ is less than 5 $J^{1/2}/cm^{3/2}$, the solubility in the organic solvent is excessively high, thus making it difficult to isolate the pyridine compound in the subsequent recrystallization step. On the other hand, the Hansen solubility parameter $\delta$ is more than 9 $J^{1/2}/cm^{3/2}$, the pyridine compound cannot be sufficiently dissolved in the dissolving step.

$$\delta^2 = 4(\delta^{d1} - \delta^{d2})^2 + (\delta^{p1} - \delta^{p2})^2 + (\delta^{h1} - \delta^{h2})^2 \quad \text{Equation (1)}$$

$\delta^d$: Energy due to dispersion force between molecules
$\delta^p$: Energy due to dipolar interaction between molecules
$\delta^h$: Energy due to hydrogen bonds between molecules For example, $\delta^{d1}$, $\delta^{p1}$, and $\delta^{h1}$ of di-tert-butyl-2,2'-bipyridine are respectively calculated as 15.6, 4.1, and 6.0, and when hexane is used as the organic solvent used in the dissolving step, $\delta^{d2}$, $\delta^{p2}$, and $\delta^{h2}$ are respectively calculated as 14.9, 0, and 0. As a result, the Hansen solubility parameter $\delta$ of hexane for the pyridine compound is calculated as 7.4 $J^{1/2}/cm^{3/2}$.

The reaction solution containing the pyridine compound synthesized through the synthesis step and the deactivation step in the reaction vessel 10 as described above is sent to a dissolution vessel 20 using a pump or the like. When normal paraffin oil (referred to as "SD solvent" hereinafter) is used as the dispersion solvent, THF is used as the reaction solvent, and ethanol is used as the deactivation liquid, the reaction solution mainly contains the SD solvent, THF, ethanol, metal alkoxide, sodium hydroxide, the unreacted monomer, and the synthesized pyridine compound.

The reaction solution sent to the dissolution vessel 20 is heated (e.g., at 80° C.) for a predetermined period of time (e.g., 10 to 20 minutes) under vacuum by a heating unit 22 to evaporate THF (with a boiling point of about 66° C.) and ethanol (with a boiling point of about 78° C.). That is, this embodiment may further include the evaporation step of evaporating the reaction solvent by heating the reaction solution in which the alkali metal has been deactivated, the evaporation step being performed prior to the dissolving step. Providing this evaporation step makes it possible to reliably dissolve the pyridine compound in the above-mentioned organic solvent without dissolving the pyridine compound in THF, which has a very small Hansen solubility parameter $\delta$ ($\delta$=4.2 $J^{1/2}/cm^{3/2}$) for the pyridine compound. It should be noted that the heating may be performed not under vacuum but under atmospheric pressure in the evaporation step, and there is no particular limitation thereto.

Next, after evaporated THF and ethanol are cooled using a cooler 21 and devolatilized, distillation treatment is performed using the difference between the boiling points of THF and ethanol, and THF is reused as the reaction solvent used in the synthesis step. Accordingly, a relatively large amount of the reaction solvent can be used efficiently, thus making it possible to reduce production cost. It should be noted that the evaporated THF and ethanol may be discarded, or molecular sieves or the like may be used to adsorb and remove only alcohol. It is preferable to use alcohol whose boiling point is significantly different from that of THF as the alcohol serving as the deactivation liquid in order to facilitate the distillation of THF. When alcohol is adsorbed and removed, it is preferable to select alcohol such as ethanol or methanol whose corresponding molecular sieve can be easily obtained.

Next, water is added to the dissolution vessel 20 under stirring to wash out the pyridine compound and the metal alkoxide attaching to the wall of the dissolution vessel 20. That is, this embodiment may further include a washing step of performing washing by adding water to the dissolution vessel 20, the washing step being performed prior to the dissolving step. It should be noted that the washing step may be performed prior to the above-described evaporation step, and there is no particular limitation thereto.

Next, an organic solvent having a Hansen solubility parameter $\delta$ of 5 $J^{1/2}/cm^{3/2}$ or more and 9 $J^{1/2}/cm^{3/2}$ or less for a pyridine compound is added to the reaction solution under stirring, and the heating unit 22 is used to perform heating to an extent that this organic solvent is not evaporated, and to dissolve the pyridine compound. A normal paraffin-based organic solvent such as hexane (with a boiling point of about 69° C.), heptane (with a boiling point of about 98° C.), or octane (with a boiling point of about 125° C.); acetone ($\delta$=6.4 $J^{1/2}/cm^{3/2}$); or the like (referred to as "normal paraffin-based organic solvent or the like" hereinafter) is used as this organic solvent, and hexane is particularly preferable because it is easily evaporated by being heated at a low temperature in the concentration step, which will be described later. Moreover, it is preferable to use a normal paraffin-based organic solvent or the like whose boiling point is significantly different from that of the dispersion solvent used in SD. The reason for this is that when hexane is evaporated and then reused, the dispersion solvent is prevented from being mixed thereinto. It should be noted that instead of water used in the washing step, the organic solvent used in the dissolving step may be injected using a injection nozzle to wash the wall.

Although the evaporation step, the washing step, and the dissolving step were carried out in the same dissolution vessel 20, separate vessels may be used to carry out steps combined as appropriate or each step. When water is used as the deactivation liquid, the washing step may be carried out in the reaction vessel 10. It should be noted that when water is used as the deactivation liquid, sodium hydroxide is produced instead of the metal alkoxide.

The reaction solution containing the pyridine compound dissolved in hexane serving as the normal paraffin-based organic solvent or the like in the dissolving step is sent to a liquid-liquid separation vessel 30 using a pump or the like. Here, the reaction solution contains the SD solvent, the metal alkoxide, sodium hydroxide, the unreacted monomer, hexane, and the pyridine compound.

Next, water is added to the liquid-liquid separation vessel 30, and an organic layer and a water layer are separated through liquid-liquid separation. That is, this embodiment includes a liquid-liquid separation step of performing liquid-liquid separation by adding water to the reaction solution, the liquid-liquid separation step being performed after the dissolving step. As a result, the metal alkoxide is decomposed into alcohol and sodium hydroxide, and the water layer constituted by water, sodium hydroxide, and an extremely small amount of alcohol, and the organic layer constituted by the SD solvent, the unreacted monomer, hexane, an extremely small amount of alcohol, and the pyridine compound are separated through liquid-liquid separation. During the liquid-liquid separation, the liquid-liquid separation vessel 30 may be stirred, or the liquid-liquid separation vessel 30 may be shaken. A molecular sieve that adsorbs and removes water and alcohol may be used to remove an extremely small amount of alcohol contained in the organic layer. It should be noted that when water is used as the deactivation liquid, alcohol is not produced, and therefore, the organic layer is constituted by the SD solvent, the unreacted monomer, hexane, and the pyridine compound.

Next, this organic layer is sent to the recrystallization step for recrystallizing the pyridine compound. At this time, the organic layer is constituted by hexane in which the SD solvent, the unreacted monomer, and the pyridine compound are dissolved. The recrystallization step includes a concentration step of concentrating hexane containing the pyridine compound by heating, a cooling step of cooling hexane containing the pyridine compound, the cooling step being performed after the concentrating step, and a filtration step of collecting the pyridine compound through filtration, the filtration step being performed after the cooling step.

First, the organic layer is sent to a concentration vessel 4 and heated (e.g., at 60° C.) for a predetermined period of time (e.g., 10 to 20 minutes) under vacuum using a heating unit 42. As a result, hexane is concentrated. It is preferable to carry out this concentration step while the organic layer is caused to flow under stirring. In particular, it is preferable to stir the organic layer using a PV mixer having discontinuous multi-stage tilted paddle blades because the concentration of the pyridine compound is made uniform. It should be noted that when the amount of hexane added to the dissolution vessel 20 is set to a minimum amount needed to recrystallize the pyridine compound, the concentration step may be omitted. A single vessel may be used as the liquid-liquid separation vessel 30 and the concentration vessel 4, and heating may be performed not under vacuum but under atmospheric pressure, and there is no particular limitation thereto.

Hexane evaporated in the concentration step may be cooled using a cooler 41 and devolatilized, and then reused as the normal paraffin-based organic solvent or the like used in the dissolving step. Accordingly, the organic solvent needed in a relatively large amount can be saved, thus making it possible to reduce production cost. It should be noted that hexane may be discarded, and there is no particular limitation thereto.

Next, the organic layer concentrated in the concentration vessel 4 is sent to a cooling vessel 5 using a pump or the like, and is cooled (e.g., at 0 to 5° C.) for a predetermined period of time. At this time, the pyridine compound contained in the organic layer subjected to the concentration step is recrystallized in an amount exceeding the saturation solubility. On the other hand, the SD solvent and the unreacted monomer remain dissolved in hexane.

Next, the organic layer sent to a filtration unit 6 is separated into the solid pyridine compound and hexane as a filtrate. This makes it possible to collect only the pyridine compound containing no other impurities. On the other hand, the filtrate may contain the residual pyridine compound that has not been recrystallized.

Figure 7:
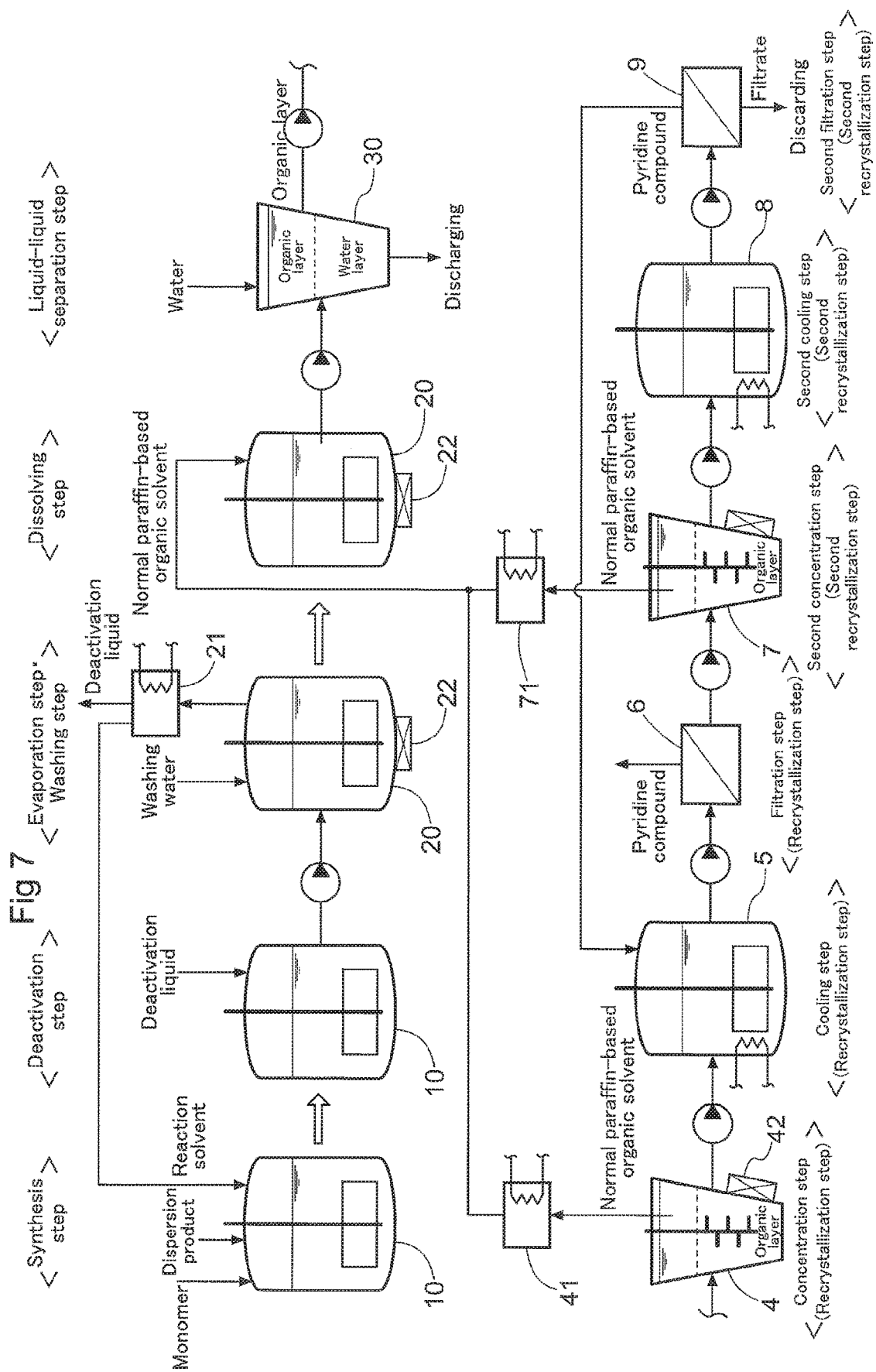
FIG. 7 is a flowchart illustrating a method for manufacturing a pyridine compound.

Therefore, as shown in FIG. 7, this embodiment may further include a second recrystallization step performed after the recrystallization step. The second recrystallization step includes a second concentration step of concentrating, by heating, a filtrate produced in the filtration step in which the pyridine compound remains, a second cooling step of cooling the filtrate, the second cooling step being performed after the second concentration step, and a second filtration step of collecting the pyridine compound through filtration, the second filtration step being performed after the second cooling step.

The filtrate obtained in the filtration step is sent to a second concentration vessel 7 using a pump or the like. In this second concentration vessel 7, the filtrate is heated (e.g., at 80° C.) for a predetermined period of time (e.g., 10 to 20 minutes) under vacuum in the same manner as in the above-described concentration vessel 4. As a result, hexane is further concentrated. It is preferable to carry out this second concentration step while the organic layer is caused to flow under stirring. In particular, it is preferable to stir the organic layer using a PV mixer having discontinuous multi-stage tilted paddle blades because the concentration of the pyridine compound is made uniform. It should be noted that heating may be performed not under vacuum but under atmospheric pressure, and there is no particular limitation thereto.

Hexane evaporated in the second concentration step may be cooled using a cooler 71 and devolatilized, and then reused as the normal paraffin-based organic solvent or the like used in the dissolving step. Accordingly, the organic solvent needed in a relatively large amount can be saved, thus making it possible to reduce production cost. It should be noted that hexane may be discarded, and there is no particular limitation thereto.

Next, the filtrate concentrated in the second concentration vessel 7 is sent to a second cooling vessel 8 using a pump or the like, and is cooled (e.g., at 0 to 5° C.) for a predetermined period of time. At this time, the pyridine compound contained in the filtrate subjected to the second concentration step is recrystallized in an amount exceeding the saturation solubility. On the other hand, the SD solvent and the unreacted monomer remain dissolved in hexane.

Next, the filtrate sent to a second filtration unit 9 is separated into the solid pyridine compound and hexane as a filtrate. The solid pyridine compound is collected, and the filtrate is discarded. This makes it possible to further improve the collection yield of the pyridine compound. On the other hand, the filtrate concentrated again contains the SD solvent in a high concentration, and therefore, there is a risk that this oil may attach to the surface of the pyridine compound. Therefore, the pyridine compound collected in the second filtration step may be mixed into the organic solvent in the cooling vessel 5. As a result, the SD solvent can be separated from the pyridine compound, thus making it possible to improve the purity. It should be noted that the pyridine compound collected in the second filtration step may be mixed in the organic solvent in the dissolution vessel 20 or the concentration vessel 4, and there is no particular limitation thereto.

Functions and Effects of this Embodiment

In the above-described embodiment, the dispersion product obtained by dispersing an alkali metal in a dispersion solvent is used, thus making it possible to synthesize a pyridine compound at low cost with reduced man-hours without using an expensive palladium catalyst, unlike a conventional method. In addition, the pyridine compound can be synthesized with high purity and a good yield.

Since the organic solvent having a Hansen solubility parameter of 5 $J^{1/2}/cm^{3/2}$ or more and 9 $J^{1/2}/cm^{3/2}$ or less for the pyridine compound is used, the pyridine compound can be easily recrystallized from this organic solvent. The reason for this is that the pyridine compound can be easily dissolved in and isolated from the organic solvent having a Hansen solubility parameter for the pyridine compound within the above-mentioned range compared with alcohol and the like having a high polarity. In addition, the pyridine compound is recrystallized not through distillation in which evaporation and condensation are performed utilizing the differences between the boiling points of various organic substances, but through cooling, and therefore, the pyridine compound can be easily separated without a large amount of labor.

On the other hand, the pyridine compound can be easily dissolved in an organic solvent such as tetrahydrofuran having a very small Hansen solubility parameter for the pyridine compound, but the solubility is excessively high, thus making it difficult to collect the pyridine compound from the reaction solvent in the recrystallization step. In addition, tetrahydrofuran dissolves in water, and therefore, there is a risk that the pyridine compound will move to the water layer. As a result, the collection yield decreases. However, as in the above-described embodiment, providing the evaporation step in which the reaction solvent is evaporated in advance makes it possible to dissolve all of the pyridine compound in the normal paraffin-based organic solvent or the like in the dissolving step. Accordingly, the collection yield of the pyridine compound can be improved.

The reaction solvent used in the synthesis step is reused, and therefore, the reaction solvent, a relatively large amount of which is required, can be prevented from being wastefully discarded, thus making it possible to reduce production cost.

The washing step is provided, and the pyridine compound and other impurities attaching to the dissolution vessel 20 are thus washed with water, thus making it possible to recrystallize the synthesized pyridine compound efficiently.

The concentration step is provided, and the recrystallization of the pyridine compound in the cooling step can be promoted. Accordingly, the collection yield of the pyridine compound in the filtration step can be improved.

The second recrystallization step is provided, and the pyridine compound is thus collected again from the filtrate obtained in the recrystallization step, thus making it possible to further improve the collection yield of the pyridine compound.

On the other hand, the organic solvent is concentrated again in the second concentration step, and therefore, the SD solvent serving as the dispersion solvent of an alkali metal and the like may attach to the surface of the pyridine compound. Accordingly, mixing the pyridine compound collected in the second filtration step again in the organic solvent in the first recrystallization step makes it possible to separate the SD solvent from the pyridine compound. As a result, the purity of the pyridine compound can be further improved.

Another Embodiment

Figure 8:
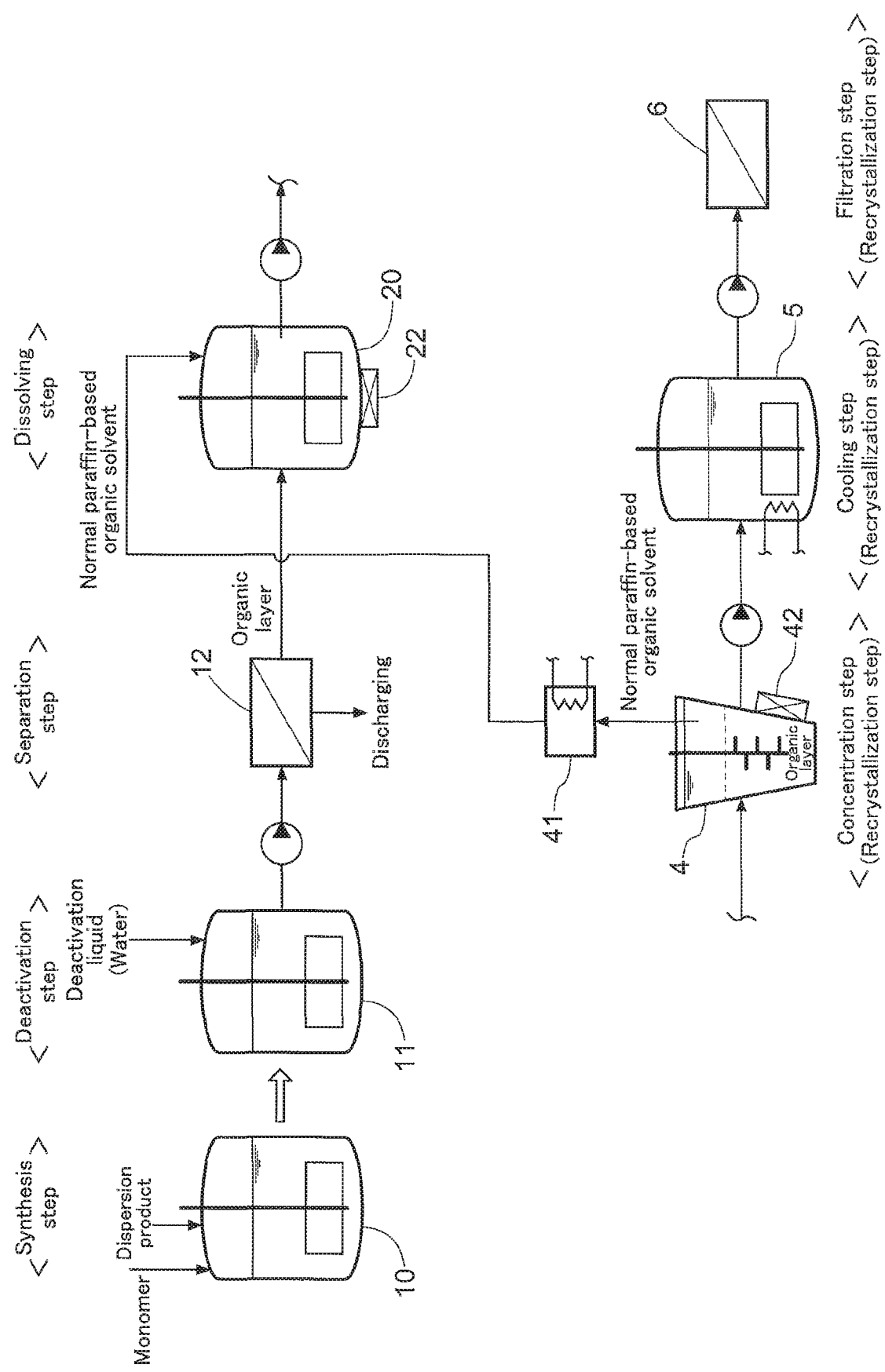
FIG. 8 is a flowchart illustrating a method for manufacturing a pyridine compound according to another embodiment.

FIG. 8 shows a flowchart illustrating a method for manufacturing a pyridine compound according to another embodiment. It should be noted that identical members are denoted by identical reference numerals and are described in order to facilitate understanding of the diagram, but there is no particular limitation thereto.

[Purification of Pyridine Compound]

In this embodiment, as shown in FIG. 8, water is used as the deactivation liquid used in the deactivation step of deactivating the alkali metal remaining after the reaction. A separation step of separating an organic layer containing the pyridine compound by filtering the reaction solution in which the alkali metal has been deactivated is performed after the deactivation step and prior to the dissolving step, and the pyridine compound is dissolved by adding an organic solvent having a Hansen solubility parameter δ of 5 $J^{1/2}/cm^{3/2}$ or more and 9 $J^{1/2}/cm^{3/2}$ or less to the separated organic layer in the dissolving step.

In the deactivation step, when THF is used as the reaction solvent, water is added to a deactivation vessel 11 such that the volume ratio of water to THF is 1 or more to deactivate the alkali metal at room temperature (e.g., 25° C.) under stirring. As a result, the alkali metal is deactivated, sodium hydroxide is generated, and THF dissolves in water. It should be noted that in this embodiment, separate vessels are used as the reaction vessel 10 and the deactivation vessel 11 to facilitate the control of operations, but a single vessel may be used as the reaction vessel 10 and the deactivation vessel 11, stirring in the deactivation vessel 11 may be omitted, and there is no particular limitation on the temperature of the deactivation vessel 11. When SD is used in the synthesis of the pyridine compound, the deactivation step may be carried out under the atmospheric environment because sodium is hydrogenized and is thus stable, but the deactivation step may be carried out in an atmosphere of inert gas, and there is no particular limitation thereto.

Next, the reaction solution containing the pyridine compound in the deactivation vessel 11 is sent to a membrane filtration apparatus 12 using a pump or the like. Here, the reaction solution mainly contains the SD solvent, THF, water, sodium hydroxide, the unreacted monomer, and the synthesized pyridine compound.

In the membrane filtration apparatus 12, the water layer constituted by water, sodium hydroxide, and THF is discharged, and the organic layer constituted by the SD solvent, the unreacted monomer, and the pyridine compound is separated. This organic layer is placed in the dissolution vessel 20, an organic solvent having a Hansen solubility parameter δ of 5 $J^{1/2}/cm^{3/2}$ or more and 9 $J^{1/2}/cm^{3/2}$ or less for the pyridine compound is added to the organic layer under stirring, and the heating unit 22 is used to perform heating to an extent that this organic solvent is not evaporated, and to dissolve the pyridine compound. A normal paraffin-based organic solvent such as hexane (with a boiling point of about 69° C.), heptane (with a boiling point of about 98° C.), or octane (with a boiling point of about 125° C.); acetone (δ=6.4 $J^{1/2}/cm^{3/2}$); or the like is used as this organic solvent, and hexane is particularly preferable because it is easily evaporated by being heated at a low temperature in the concentration step, which will be described later. Moreover, it is preferable to use a normal paraffin-based organic solvent or the like whose boiling point is significantly different from that of the SD solvent. The reason for this is that when hexane is evaporated and then reused, the dispersion solvent is prevented from being mixed thereinto.

Next, the organic layer dissolved in hexane is sent to the recrystallization step of recrystallizing the pyridine compound. The subsequent recrystallization step and second recrystallization step are the same as those in the above-described embodiment, and therefore, detailed description thereof will be omitted.

In the separation step of this embodiment, the organic layer containing the pyridine compound is separated in the state in which THF is separate in the filtrate. As a result, the evaporation step of evaporating THF, the liquid-liquid separation step, and the like can be omitted, thus making it possible to simplify the purification process of the pyridine compound.

Other Embodiments (1) Although the recrystallization step is performed twice in the above-described embodiment, the recrystallization step may be performed only once or three times or more.

(2) The order of the steps of the above described embodiment may be changed as appropriate, or some of them may be omitted, without departing from the spirit or essential characteristics of the present invention.

INDUSTRIAL APPLICABILITY

The present invention can be used in all technical fields utilizing a pyridine compound, particularly in the manufacture of organic EL materials, pharmaceuticals, agricultural chemicals, dyes, and the like, and in the carbon dioxide reduction reaction.

REFERENCE SIGNS LIST

20 Dissolution vessel
δ Hansen solubility parameter

The invention claimed is:

1. A method for synthesizing a di-tert-butyl-2,2'-bipyridine compound represented by Formula (I)

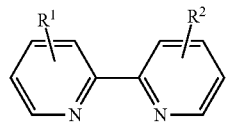

Formula (I)

where $R^1$ and $R^2$ are independently tert-butyl groups, comprising a step of
reacting, in a reaction solvent selected from the group consisting of ether-based solvent, normal paraffin-based solvent, aromatic solvent, amine-based solvent, heterocyclic compound solvent, and mixed solvent thereof, a tert-butylpyridine compound with a dispersion of particles of sodium in a solvent selected from the group consisting of aromatic solvent, normal paraffin-based solvent, and mixed solvent thereof.

2. The method for synthesizing a bipyridine compound according to claim 1, wherein a hydrogen donor is added to a reaction product produced through the reaction of the tert-butylpyridine compound with the dispersion product obtained by dispersing an alkali metal in a dispersion solvent.

3. The method for synthesizing a bipyridine compound according to claim 1, wherein the reaction solvent contains a hydrogen donor.

4. The method for synthesizing a bipyridine compound according to claim 1, wherein the tert-butylpyridine compound is 4-tert-butylpyridine, and 4,4'-di-tert-butyl-2,2'-bipyridine is synthesized.

5. A The method for synthesizing a bipyridine compound represented by Formula (I)

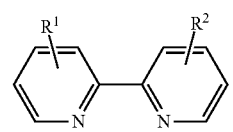

Formula (I)

where $R^1$ and $R^2$ are independently tert-butyl groups, comprising a step of
reacting, in a reaction solvent including tetrahydrofuran, a tert-butylpyridine compound with a dispersion of particles of sodium in a solvent selected from the group consisting of aromatic solvent, normal paraffin-based solvent, and mixed solvent thereof, wherein
when a ratio of the tetrahydrofuran with respect to 1 mmol of the tert-butylpyridine compound is set to 2 ml or more and 8 ml or less, and the particles of sodium are used in an amount of 1 mol equivalent or more and 2.5 mol equivalents or less with respect to the tert-butylpyridine compound.

6. The method for synthesizing a bipyridine compound according to claim 1, wherein the particles of sodium have an average particle diameter of less than 10 μm.

7. The method for synthesizing a bipyridine compound according to claim 1, wherein the reaction solvent and dispersion solvent are separate from one another.

8. The method for synthesizing a bipyridine compound according to claim 1, wherein the reaction solvent includes tetrahydrofuran.

* * * * *